(12) United States Patent
Manley

(10) Patent No.: US 8,834,409 B2
(45) Date of Patent: Sep. 16, 2014

(54) METHOD FOR ABLATION VOLUME DETERMINATION AND GEOMETRIC RECONSTRUCTION

(75) Inventor: Prakash Manley, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 893 days.

(21) Appl. No.: 12/434,903

(22) Filed: May 4, 2009

(65) Prior Publication Data

US 2010/0030208 A1   Feb. 4, 2010

Related U.S. Application Data

(60) Provisional application No. 61/084,489, filed on Jul. 29, 2008.

(51) Int. Cl.
*A61B 18/04* (2006.01)
*A61B 18/18* (2006.01)
*G01N 33/50* (2006.01)

(52) U.S. Cl.
CPC ............ *G01N 33/5091* (2013.01); *A61B 18/18* (2013.01); *A61B 18/1815* (2013.01)
USPC .......................................... 604/32; 604/501

(58) Field of Classification Search
USPC ............ 606/32, 27, 28, 41; 604/500–522, 21, 604/22, 57–64
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,798,215 A | 1/1989 | Turner | |
| 5,097,844 A | 3/1992 | Turner | |
| 5,417,210 A | 5/1995 | Funda et al. | |
| 5,588,432 A | 12/1996 | Crowley | |
| 5,688,267 A | 11/1997 | Panescu et al. | |
| 5,943,719 A | 8/1999 | Feldman et al. | |
| 6,022,346 A | 2/2000 | Panescu et al. | |
| 6,031,375 A | 2/2000 | Atalar et al. | |
| 6,053,912 A | 4/2000 | Panescu et al. | |
| 6,056,745 A | 5/2000 | Panescu et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Kevin C Sirmons
*Assistant Examiner* — Phillip Gray

(57) ABSTRACT

A method for determining a volume of ablated tissue is provided. The method includes the steps of: supplying energy to tissue to create an ablation volume therein; excising one or more slices of the tissue having a portion of the ablation volume therein; and subjecting at least a portion of the slice to a first contrast agent for a predetermined period of time, wherein the contrast agent is configured to color dead cells within the ablation volume.

8 Claims, 3 Drawing Sheets

(56) References Cited

U.S. PATENT DOCUMENTS

| | | | |
|---|---|---|---|
| 6,241,725 B1 | 6/2001 | Cosman | |
| 6,289,279 B1 | 9/2001 | Ito et al. | |
| 6,375,606 B1 | 4/2002 | Garibaldi et al. | |
| 6,478,793 B1 | 11/2002 | Cosman et al. | |
| 6,506,189 B1 | 1/2003 | Rittman, III et al. | |
| 6,512,956 B2 | 1/2003 | Arndt et al. | |
| 6,530,922 B2 | 3/2003 | Cosman et al. | |
| 6,575,969 B1 | 6/2003 | Rittman, III et al. | |
| 6,592,579 B2 | 7/2003 | Arndt et al. | |
| 6,603,994 B2 | 8/2003 | Wallace et al. | |
| 6,675,050 B2 | 1/2004 | Arndt et al. | |
| 6,725,080 B2 | 4/2004 | Melkent et al. | |
| 6,821,274 B2 * | 11/2004 | McHale et al. | 606/41 |
| 6,944,504 B1 | 9/2005 | Arndt et al. | |
| 7,166,105 B2 | 1/2007 | Mulier et al. | |
| 7,218,958 B2 | 5/2007 | Rashidi | |
| 7,282,049 B2 | 10/2007 | Orszulak et al. | |
| 7,294,143 B2 | 11/2007 | Francischelli | |
| 7,306,595 B2 | 12/2007 | Ostrovsky et al. | |
| 7,364,579 B2 | 4/2008 | Mulier et al. | |
| 7,367,974 B2 | 5/2008 | Haemmerich et al. | |
| 7,392,077 B2 | 6/2008 | Mueller et al. | |
| 7,410,486 B2 | 8/2008 | Fuimaono et al. | |
| 7,416,552 B2 | 8/2008 | Paul et al. | |
| 7,419,489 B2 | 9/2008 | Vanney et al. | |
| 7,439,736 B2 | 10/2008 | Meaney et al. | |
| 7,467,015 B2 | 12/2008 | Van der Weide | |
| 7,480,533 B2 | 1/2009 | Cosman et al. | |
| 7,565,207 B2 | 7/2009 | Turner et al. | |
| 7,769,432 B2 * | 8/2010 | Klimberg et al. | 600/473 |
| 2002/0022836 A1 | 2/2002 | Goble et al. | |
| 2004/0097805 A1 | 5/2004 | Verard et al. | |
| 2004/0242992 A1 | 12/2004 | Hareyama | |
| 2006/0079887 A1 | 4/2006 | Buysse et al. | |
| 2007/0250054 A1 | 10/2007 | Drake | |
| 2008/0021448 A1 | 1/2008 | Orszulak et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 3/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 645 234 | 4/2006 |
| EP | 1 645 235 | 4/2006 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO 94/28391 | 12/1994 |
| WO | WO 96/34571 | 11/1996 |
| WO | WO97/41924 | 11/1997 |
| WO | WO97/43971 | 11/1997 |
| WO | WO 99/04710 | 2/1999 |
| WO | WO 00/43027 | 7/2000 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.

(56) References Cited

OTHER PUBLICATIONS

International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" in William RH, Rengachary SS (eds): Neurosurgery, New York: McGraw-Hill, vol. 111, (1984), pp. 2490-2499.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical 1mpedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.

(56) References Cited

OTHER PUBLICATIONS

Herman at al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . ." Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/1977).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Oapril 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No.4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817.825.

S. Humphries Jr. et al., "Finite•Element Codes to Model Electrical Heating and Non•Llnear Thermal Transport In Biological Media", Proc. ASME HTD-355, 131 (1997).

Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation-'COA-COMP" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report Ep 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.

* cited by examiner

METHOD FOR ABLATION VOLUME DETERMINATION AND GEOMETRIC RECONSTRUCTION

CROSS-REFERENCE TO RELATED APPLICATIONS

This application claims the benefit of priority to U.S. Provisional Application Ser. No. 61/084,489 entitled "METHOD FOR ABLATION VOLUME DETERMINATION AND GEOMETRIC RECONSTRUCTION" filed Jul. 29, 2008 by Prakash Manley, which is incorporated by reference herein.

BACKGROUND

1. Technical Field

The present disclosure relates to electrosurgical apparatuses, systems and methods. More particularly, the present disclosure is directed to a system and method for determining the volume of an ablation lesion after a tissue ablation procedure utilizing electrosurgical electrodes.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In the case of tissue ablation, radiofrequency electrical current or microwave energy is applied to a targeted tissue site to create an ablation volume. The resulting ablation volume may then be observed and various ablation metrics may be measured and recorded. Conventional methods of obtaining ablation metrics include recording the small diameter, large diameter, and height of the ablated tissue to calculate the volume. Typically, these three parameters are input for the equation for ellipsoidal volume to calculate an approximate ablation volume. Conventional methods such as this often provide inexact measurements, inconsistent recordings, as well as inaccurate reporting of achieved volumes. Further, conventional methods of volumetric calculation lack evaluative tools such as determining the effect of adjacent structures on the ablation volume, qualifying the completeness of the ablation volume, predicting specific volumes and/or shapes based on a given energy applicator configuration.

SUMMARY

The present disclosure relates to a method for determining a volume of an ablation lesion. The method includes the steps of: supplying energy to tissue to create an ablation volume therein; excising one or more slices of the tissue having a portion of the ablation volume therein; and subjecting at least a portion of the slice to a first contrast agent for a predetermined period of time, wherein the contrast agent is configured to color dead cells within the ablation volume.

A method for determining a volume of an ablation lesion is also contemplated by the present disclosure. The method includes the steps of: supplying energy to tissue to create an ablation volume therein; excising one or more slices of the tissue having a portion of the ablation volume therein; subjecting at least a portion of the slice to a first contrast agent for a predetermined period of time, wherein the contrast agent is configured to color dead cells within the ablation volume. The method also includes the steps of rinsing the slice with a rinse solution to remove any superficial attachment of contrast agent from live cells and drying the slice to remove the rinse solution and the first contrast agent.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for a system and method for determining a volume of an ablation lesion and providing a geometric reconstruction of the ablation volume. The ablation lesion may be created by applying any suitable energy, such as radiofrequency ("RF"), microwave, electrical, ultrasound, heat, cryogenic, and laser. For the purposes of illustration, the following description discusses formation of the ablation use via the application of RF energy and corresponding electrosurgical ablation electrodes to create ablation lesions in accordance with embodiments of the present disclosure. Those skilled in the art will appreciate that corresponding instruments may have to be utilized based on the type of suitable energy being utilized.

Size and shape of ablation volumes is primarily dependent on the thermal spread and energy flow patterns. In addition, ablation volume is also dependent on the type of tissue being ablated as well as tissue's inherent conductivity and dielectric properties, which govern the thermal spread and energy flow therethrough. The type of energy being used in ablation (e.g., RF, microwave, etc.) may also have a bearing on the patterns of cell death and apoptosis. Thermal injury begins at 41° C. with time of the heat exposure required for complete cell death exponentially decreasing above 42.5° C. (See Dickson J. A., Caldewood S. K., Temperature Range and Selective Sensitivity of Tumors to Hyperthermia: A Critical Review, *Ann. N. Y. Acad. Sci.,* 1980, Vol. 335, pp. 180-205, Rhee J. G., Song C. W., Thermotolerance of Organized Tissues and Tumors. In: Henle K J, ed., *Thermotolerance*. Vol. 1, Boca Raton, Fla.; CRC Press Inc., 1987, pp. 73-95.) Apoptosis may be seen at temperature below 46° C. with necrosis beyond this threshold. (See Liu F. F., Wilson B. C., Hyperthermia and Photodynamic Therapy. In: Tannock I F, Hill R P, eds., *The Basic Science of Oncology*, New York, N.Y.; McGraw-Hill Book Co.; 1998; pp. 443-453.). Correlating an accurately modeled temperature profile or tissue property profile with viability and apoptosis assays for determining ablation volume may be used for instantaneous real-time determination of ablation volume.

Figure 1:
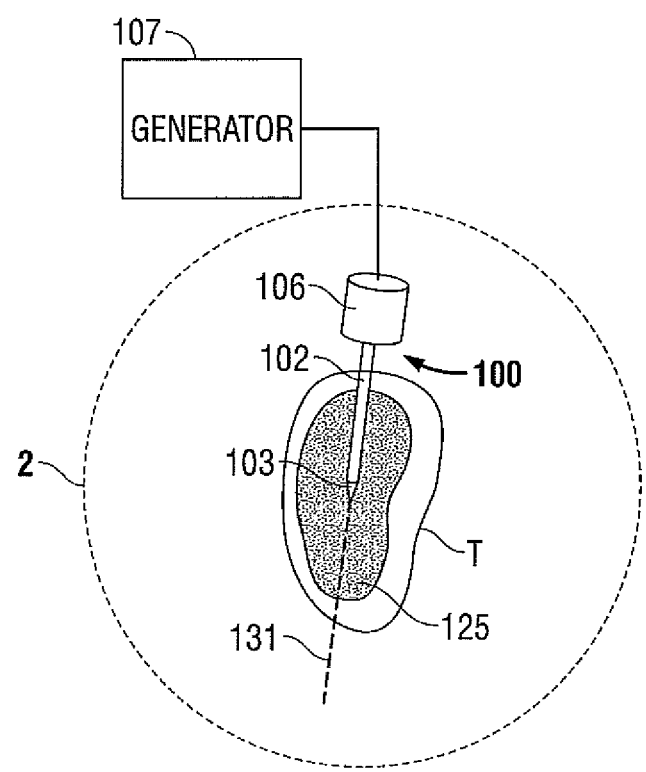
FIG. 1 shows an embodiment of an electrosurgical system for tissue ablation, measuring ablation volume, and displaying image scan data.

Referring to FIG. 1, an ablation electrode 100 is shown having an insulated shaft 102 and an electrically exposed tip 103. Electrode 100 may be, for example, a high frequency or RF thermo-ablation electrode configured to be placed in the body of a patient (not explicitly shown) so that the tip 103 is near a target tissue "T", such as a cancerous tumor or other tissue structure within the body. A hub or junction connector element illustrated schematically by 106 may be any suitable type of connection device, such as jacks, hoses, ports, etc. that connect the RF electrode to a power source, such as a radiofrequency (RF) or microwave generator 107. The generator 107, according to embodiments of the present disclosure, can perform monopolar and bipolar electrosurgical procedures, including tissue ablation procedures (e.g., RF or microwave). Further, the generator may include suitable electronic circuitry configured for generating radio frequency power specifically suited for ablation, as well as other electrosurgical modes (e.g., cutting, blending, division, etc.) and procedures (e.g., monopolar, bipolar, vessel sealing, tissue ablation).

Figure 2:
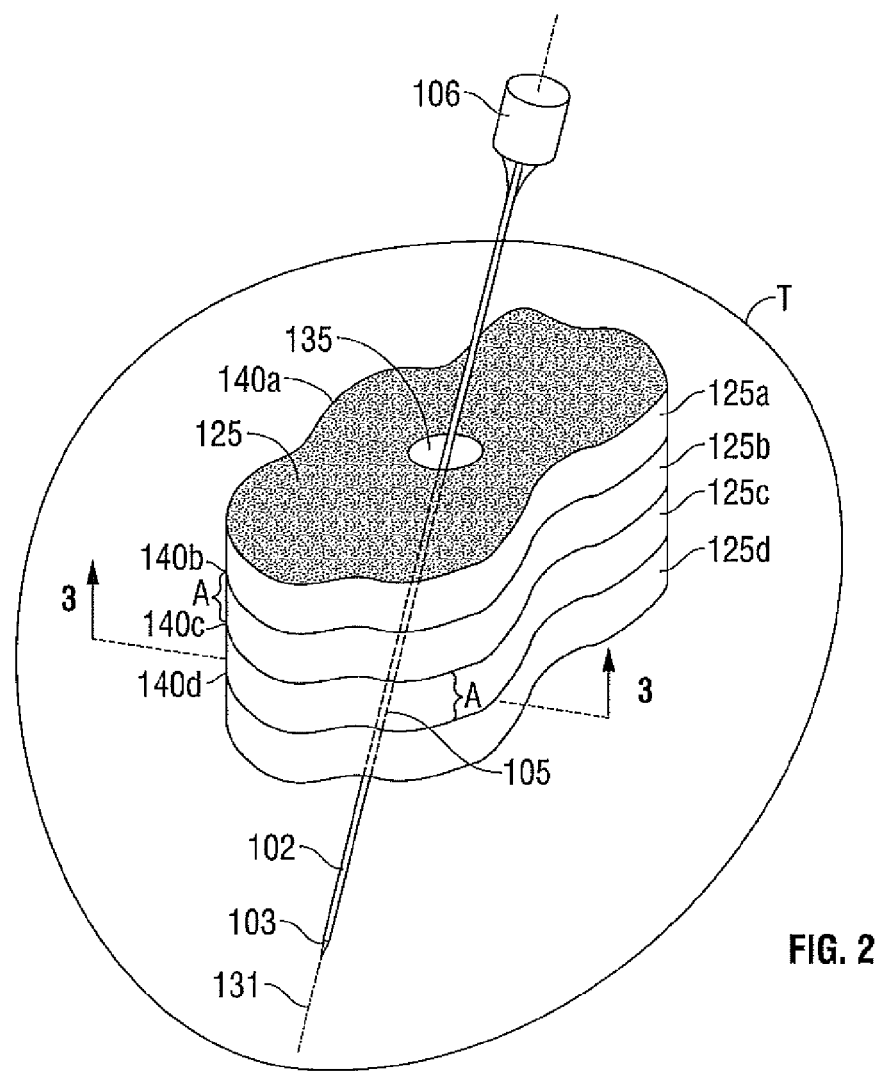
FIG. 2 shows an electrode defining a path through tissue for heating ablation.

With reference to FIG. 2, the electrode 100 is shown being inserted through the tissue "T" at a trajectory or path 131. Electrode 100 is used to create an ablation lesion defined by an ablation volume 125 within the tissue "T" by heating tissue via application of energy from the generator 107 to the tissue. Path 131 may also be defined as an axis of electrode 100 through ablation volume 125. Path 131 of electrode 100 through volume 125 provides a trajectory reference or point 135 from which volumetric calculations may be made for volume 125, as will be discussed in further detail below.

Figure 3:
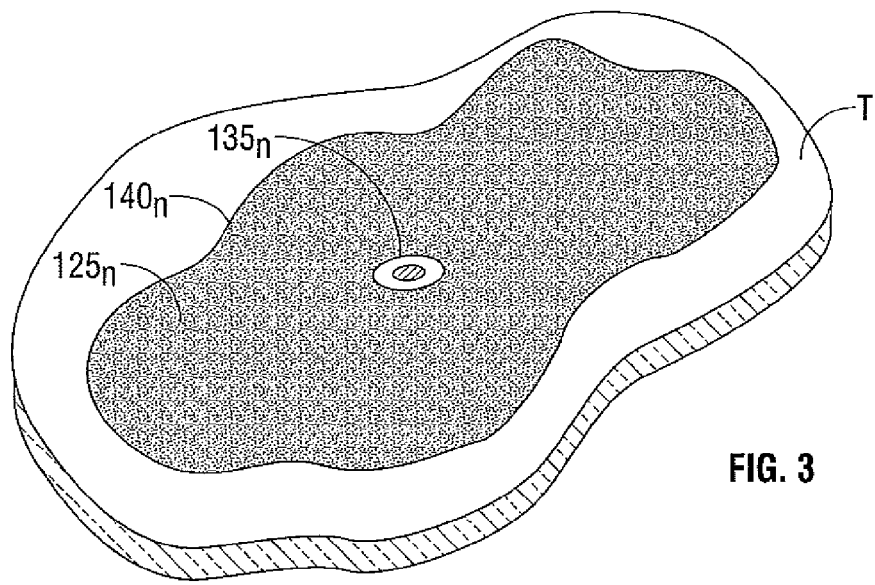
FIG. 3 shows a sliced segment of the tissue of FIG. 2.

Once the ablation volume 125 is created, a segment of the tissue "T" encompassing the ablation volume 125 is excised. Volume 125 may be deconstructed into a plurality of slices, depicted here as 125a, 125b, 125c, and 125d, for analyzing the boundaries of the ablation volume 125. This enables volumetric determination of volume 125 and, further, graphical representation on a display (not explicitly shown). FIG. 3 shows a cross-sectional view of any slice $125_n$ of the plurality of slices 125a-125d indicated by line 3-3 in FIG. 2. Each of the plurality of slices $125_n$ defines a cross-sectional perimeter $140_n$ generally concentric about trajectory point $135_n$.

In certain situations, the boundary between destroyed tissue of the ablation volume 125 and viable tissue along the sectional perimeter 140n of the surrounding tissue T is defined poorly. Thus, the present disclosure provides for a method to provide added contrast between the ablated tissue and the viable to better define the boundary between the ablation volume 125 and the tissue T. In one embodiment, after the ablation volume 125 is excised and one or more cross-sectional slices 125n thereof are obtained, a stain, a dye or another type of a cytometric contrast agent is applied to the slice.

Suitable contrast agents for use as a stain include nitro-blue tetrazolium, hematoxylin and eosin stains, reduced dihydropyridine nucleotide, fluorescent dyes such as calcein AM and ethidium homodimer, available from Invitrogen Corp. of Carlsbad, Calif., which may be used with an anti-fading agent such as ProLong® Gold Antifade Reagent also available from Invitrogen Corp. of Carlsbad, Calif. In one embodiment, the contrast agent may be trypan blue, which is a suitable viability marker that stains dead cells a blue color useful for ablation boundary demarcation.

Contrast agents are difficult to use with three-dimensional arrangement of parenchymal tissue due to the fact that irrelevant background material such as extra-cellular matrix, collagen and serum are also stained by the contrast agents. The present disclosure provides for a method which allows for use of contrast agents with parenchymal tissue (e.g., liver) to identify the ablation volume 125. The stain is applied to one or more cross-sectional slices of the tissue "T" enclosing the ablation volume 125. The magnitude of background staining is controlled by limiting the staining period to a predetermined period of time and thereafter rinsing the contrast agents from the slices of the tissue "T." The contrast agents stain the dead tissue, while the viable tissue is unstained after the rinse. The rinsed slices are then dried to further remove any residual stain from the viable tissue to obtain a clear demarcation between ablated stained tissue and viable unstained tissue. As a result, the tissue within the ablated volume 125 appears a different color (e.g., blue) from the natural tissue color of surrounding viable tissue (e.g., red). Due to rapid deterioration of tissue and staining contrast, the stained slices may be imaged immediately (e.g., photographed, scanned, etc.) to capture the demarcation of the ablation volume 125 for later analysis.

Figure 4:
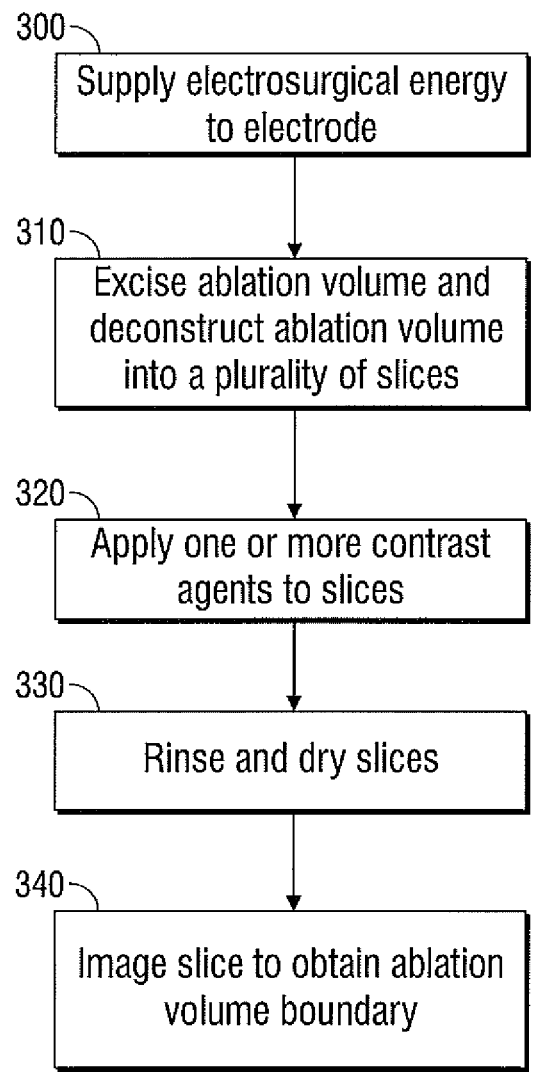
FIG. 4 illustrates a method for determining an ablation volume according to embodiments of the present disclosure.

A method for volumetric determination of boundaries of the ablation volume 125 according to embodiments of the present disclosure will now be described with reference to FIG. 4 in conjunction with FIGS. 2 and 3. In step 300, electrosurgical energy is supplied from the RF generator 107 to the electrode 100. As illustrated in FIG. 2, electrode 100 is used to create an ablation lesion by heating volume 125 via application of RF energy from the generator 107 to volume 125.

In step 310, ablation volume 125 is excised from the tissue "T" and is cut or "sliced" substantially perpendicular to trajectory point 135 into a plurality of slices 125a-125d. The slices may be of any desired thickness. In one embodiment, the slices may be about 0.5 cm thick to allow for the slices to be placed on plate scanner to obtain a digital image thereof.

In step 320, one or more of the slices 125a-125d are stained by a contrast agent to demarcate the boundary between the dead cells of the ablation volume 125 and the viable cells of the surrounding tissue "T." Staining may be performed by submerging the slice 125n in a contrast agent solution for a predetermined period of time form about 1 minute to about 5 minutes. The contrast agent penetrates cellular walls of dead cells of the ablation volume 125 while having no effect on viable tissue surrounding the ablation volume, thereby coloring the ablation volume 125 a color (e.g., blue) different from the viable tissue. This provides a clear contrast between the ablation volume 125 and the remaining viable tissue.

To prevent the coloring of the viable tissue, in step 330, the slice 125n is rinsed by a solution (e.g., a phosphate buffered saline solution) to remove any superficial attachment of the contrast agent from the cells. In addition, the slice 125n is dried to remove the rinse solution and the contrast agent. This may be accomplished by using an absorbent material (e.g., cloth, paper towel, etc.) to remove the solutions from the slice 125n.

In step 340, the contrasted slice 125n is imaged, by scanning, by photographing, etc., to capture the colored ablation volume 125. This allows for subsequent evaluation of the ablation volume 125, such as depth, size, etc. More specifically, with reference to FIG. 2, a thickness, indicated in FIG. 2 as "A," and a cross-sectional perimeter 140a-140d for each of the plurality of slices 125a-125d may be determined. Cross-sectional perimeters 140a-140d for each of the plurality of slices 125a-125d are derived based on the contrasted image of the ablation zone.

The volume of each of the plurality of slices 125a-125d may also be determined. Any suitable method for determining volume may be used, such as, for example, the contour or perimeter method. In addition, the volume of the ablation volume 125 may be determined based on volumetric data of each of the slices 125*n* individually and then modeled to obtain the shape of the volume as defined on each slice. Cross sectional perimeter 140*a*-140*d* for each slice 125*a*-125*d* may be used to determine the volume. Alternatively, for each slice 125$_n$, thickness "A" may be multiplied by the perimeter area of that particular slice to determine the slice volume. This determination is carried out for each of the plurality of slices 125*a*-125*d*. The volume determinations derived for each of the plurality of slices 125*a*-125*d* are then summed to yield an ablation volume. In this manner, an accurate volumetric determination is made rather than approximated calculations yielded by conventional and/or presently competing volumetric calculation methods.

EXAMPLE

Trypan blue staining. An ablation lesion was created in porcine liver tissue. The ablation lesion was then excised and sliced into cross-sectional slices. A staining solution of trypan blue (0.4% trypan blue, 0.81% sodium chloride, 0.06% potassium phosphate dibasic) from Sigma-Aldrich of St. Louis, Mo. was placed in a beaker placed under a fume hood. The slice, with a pertinent surface containing a segment of the ablation volume was exposed to the solution in the beaker for approximately 5 minutes. The slice was then removed and was washed vigorously in a rinsing solution of 1× phosphate buffered saline solution. The rinsed and stained slice was then dried by absorbing the staining and rinsing solutions. The dried slice was then imaged by scanning the slice. The staining procedure was repeated for each of the slices of the ablated lesion.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for determining a volume of ablated tissue comprising the steps of:
   inserting an electrode into tissue, a longitudinal axis of the electrode defining a path of the electrode;
   supplying energy via the electrode to tissue to create an ablation volume therein;
   excising a plurality of slices of the tissue having at least a portion of the ablation volume therein, each of the plurality of slices having a thickness, a cross-sectional perimeter, and a trajectory point defined by the path of the electrode;
   subjecting the plurality of the slices to a first contrast agent for a predetermined period of time, wherein the contrast agent is configured to color dead cells within the ablation volume;
   rinsing the plurality of the slices with a rinse solution to remove any superficial attachment of the contrast agent from live cells of the tissue;
   drying the plurality of the slices to remove the rinse solution and the first contrast agent;
   determining a volume of each of the plurality of slices based on the trajectory point, the cross-sectional perimeter, and the thickness of each slice of the tissue; and
   summing the volumes from each of the plurality of slices to obtain the volume of ablated tissue.

2. The method according in claim 1, wherein the energy of the supplying step is selected from the group consisting of radio frequency and microwave.

3. The method according in claim 1, wherein the energy of the supplying step is supplied to at least one electrode.

4. The method according to claim 1, further comprising the step of:
   forming a solution having the contrast agent; and
   submerging at least a portion of each of the plurality of the slices to the solution.

5. The method according to claim 1, wherein the rinse solution of the rinsing step is 1× phosphate buffered saline solution.

6. The method according to claim 1, wherein the first contrast agent of the subjecting step is trypan blue.

7. The method according to claim 1, wherein the predetermined period of the subjecting step is about 5 minutes.

8. A method for determining a volume of ablated tissue comprising the steps of:
   inserting an electrode into tissue, a longitudinal axis of the electrode defining a path of the electrode;
   supplying energy to tissue to create an ablation volume therein;
   excising a plurality of slices of the tissue having at least a portion of the ablation volume therein, each of the plurality of slices having a thickness, a cross-sectional perimeter, and a trajectory point defined by the path of the electrode;
   controlling a magnitude of background staining of at least a portion of the slice in order to identify a boundary of the volume of ablated tissue by limiting a staining period of time with respect to a contrast agent applied to the at least a portion of the slice to a predetermined period of time and thereafter rinsing the contrast agent from the at least a portion of the slice; and
   determining a volume of each of the plurality of slices based on the trajectory point, the cross-sectional perimeter, and the thickness of each slice of the tissue; and
   summing the volumes from each of the plurality of slices to obtain the volume of ablated tissue.

* * * * *